United States Patent [19]

Holloway et al.

[11] Patent Number: 4,937,267

[45] Date of Patent: Jun. 26, 1990

[54] METHOD OF TREATMENT OF OBESITY

[75] Inventors: Brian R. Holloway, Congleton; Ralph Howe, Macclesfield; Balbir S. Rao, Holmes Chapel; Donald Stribling, Prestbury, all of England

[73] Assignee: Imperial Chemical Industries PLC, London, England

[21] Appl. No.: 24,145

[22] Filed: Mar. 10, 1987

[30] Foreign Application Priority Data

Mar. 25, 1986 [GB] United Kingdom ............... 8607312

[51] Int. Cl.$^5$ ................ A61K 31/16; A61K 31/165; C07C 103/34

[52] U.S. Cl. ............................ 514/630; 514/629; 564/220

[58] Field of Search ............ 564/220; 514/629, 630

[56] References Cited

U.S. PATENT DOCUMENTS

| | | | |
|---|---|---|---|
| 3,928,412 | 12/1975 | Smith et al. | 564/220 X |
| 3,933,911 | 1/1976 | Main | 514/630 |
| 3,959,369 | 5/1976 | Smith | 564/220 X |
| 3,961,072 | 6/1976 | Cox et al. | 514/629 X |
| 4,010,189 | 3/1977 | Smith | 564/220 X |
| 4,083,992 | 4/1978 | Smith | 564/220 X |
| 4,085,136 | 4/1978 | Tucker | 564/220 X |
| 4,396,627 | 8/1983 | Ainsworth et al. | 514/630 X |
| 4,618,624 | 10/1986 | Asato | 514/629 X |

FOREIGN PATENT DOCUMENTS

| | | | |
|---|---|---|---|
| 2253776 | 5/1973 | Fed. Rep. of Germany | 564/220 |
| 1455116 | 11/1976 | United Kingdom | 564/220 |

*Primary Examiner*—Floyd D. Higel
*Attorney, Agent, or Firm*—Cushman, Darby & Cushman

[57] ABSTRACT

A method of treatment of obesity or diabetes mellitus in a warm-blooded animal requiring such treatment which comprises administering to said animal an effective amount of the compound N-(2-[2-hydroxy-3-phenoxypropyl]aminoethyl)-isobutyramide in racemic (R,S) or levorotatory optically active (S) form, or of a pharmaceutically acceptable acid-addition salt thereof.

7 Claims, No Drawings

METHOD OF TREATMENT OF OBESITY

The invention concerns novel therapeutic agents having thermogenic properties for use in the treatment of obesity and/or related conditions such as diabetes mellitus especially of maturity onset, in warm-blooded animals such as man. More particularly, the invention provides a new method of treatment of obesity and/or related conditions involving administration of a known pharmaceutical agent and the use of said agent in the manufacture of a novel medicament.

According to the invention there is provided a method of treatment of obesity and/or a related condition affecting a warm-blooded animal which comprises administering to said animal an effective amount of the compound N-(2-[2-hydroxy-3-phenoxypropyl]aminoethyl)isobutyramide of formula I (set out hereinafter) in racemic (R,S) or laevorotatory optically active (S) form, or a pharmaceutically acceptable acid-addition salt thereof.

The invention also provides the use of the compound of formula I in racemic (R,S) or laevorotatory optically active (S) form, or of a pharmaceutically acceptable salt thereof, in the manufacture of a novel medicament for the treatment of obesity and/or related conditions in warm-blooded animals, including man.

It will be understood that "treatment" includes prophylactic as well as therapeutic use. It will also be understood that the term laevorotatory optically active form means the form having negative specific optical rotation measured in methanol at a wavelength of 589 nm i.e. at the D line of the sodium vapour emission spectrum.

The racemic (R,S) form of the compound of formula I is described, inter alia, as its free base as a cardioselective beta-adrenergic blocking agent in our UK patent specification Ser. No. 1455116, as are the oxalate and 2,3:4,6-di-O-isopropylidene-$\alpha$-D-xylo-hexulosofuranosonate salts of the corresponding (−)- (or laevorotatory) optically active (S) form. The preparation of the crystalline free base form of the latter, laevorotatory optically active form of the compound of formula I and the crystalline hydrochloride salt thereof has not hitherto been described and is set out in the accompanying Preparations.

The compound of formula I will generally be used in accordance with the invention in the form of a suitable conventional pharmaceutical composition for administration to man. Such a composition may be made by methods well known in the art using conventional, pharmaceutically acceptable excipients. Suitable compositions include, for example, those described in UK patent specification, Ser. No. 1455116.

Similarly, for administration to other obese warm-blooded animals, such as cats or dogs, the compound of formula I will generally be used as a conventional, veterinary composition together with a veterinarily acceptable diluent or carrier.

An example of a suitable pharmaceutically acceptable acid-addition salt is, for example, a hydrohalide salt such as a hydrochloride or hydrobromide, or a salt with a suitable organic acid, such as a citrate or D-gluconate salt.

In general, it is preferred to use the laevorotatory optically active (S) form of the compound of formula I, that is (S)-N-(2-[2-hydroxy-3-phenoxypropyl]aminoethyl)isobutyramide, as the free base, or as a pharmaceutically acceptable acid-addition salt thereof, in the methods of the invention. The compound of formula I may be obtained in laevorotatory optically active form by resolution of the racemic form with 2,3:4,6-di-O-isopropylidene-$\alpha$-D-xylo-hexulofuranosonoic acid, using the procedure described in UK patent specification Ser. No. 1455116, followed by the production of the novel free base and hydrochloride salt form of the laevorotatory optically active form of the compound of formula I as described in the accompanying preparations. Alternatively, the (S)-form may be prepared directly by reaction of (S)-1,2-epoxy-3-phenoxypropane with N-(2-aminoethyl)isobutyramide in conventional manner, for example as described in the accompanying preparations.

The use of the compound of formula I in the treatment of obesity and/or related conditions is based on the capability of the compound to increase thermogenesis. Thus, the activity of the compound may be demonstrated, for example, by assessing the effects on thermogenesis, carcass composition and/or on obesity in warm blooded animals.

The thermogenic effects of the compound of formula I may be demonstrated in laboratory animals using the following standard tests:

(a) Rats are cold adapted by being placed in a cold environment (4° C.) for 10 days in order to increase their capacity for thermogenesis. They are then transferred to a thermoneutral environment (29° C.). Three hours later the core temperature is measured to determine a base-line reading and the test compound is administered sub-cutaneously or orally as a solution or suspension in 0.45% w/v aqueous sodium chloride, 0.25% w/v Polysorbate 80. After one hour, the core temperature is again measured. In this test a compound which causes a statistically significant increase in the core temperature of >0.3° C. at a dose of 15 mg/kg or less is considered to be significantly active. This test acts as a model for the depressed thermogenesis which occurs during dieting.

(b) Rats are cold adapted at 4° C. for 4 days to increase their capacity for thermogenesis. They are then transferred to a warm environment at 23° C. for 2 days. On the following day, the test compound is administered sub-cutaneously or orally as described in (a). Animals are sacrificed one hour later and the interscapular brown adipose tissue (BAT) pad removed. BAT mitochondria are prepared by differential centrifugation and GDP binding determined (Holloway et al., *International Journal of Obesity*, 1984, 8, 295) as a measure of thermogenic activation. Each test includes a control which is dosed with the solution/suspension vehicle only and a positive control which is dosed with isoprenaline (as its sulphate) at 1 mg/kg. Test compounds are routinely dosed at 0.1, 1.0 and 10 mg/kg and results expressed in terms of the effect on GDP binding produced by isoprenaline. From these results, a dose ($ED_{50}$) necessary to produce 50% of the isoprenaline effect is calculated by linear regression analysis. Compounds are considered active in this test if they cause a significant elevation in GDP binding as compared to controls. This test serves to indicate that the thermogenic effects observed in test (a) are mediated through an increase in effect on BAT rather than by some non-specific or toxic mechanism.

(c) Rats are adapted to a thermoneutral environment (29° C.) for 2 weeks in order to decrease their capacity for BAT mediated non-shivering thermogenesis. During the final 3 days the animals are accustomed to use an apparatus for measuring heart rate non-invasively via foot-pad electrodes connected to an ECG integrator giving a continuous read-out of heart rate. A test compound is administered sub-cutaneously at the $ED_{50}$ determined in test (b), and heart rate determined after 15 minutes. The procedure is then repeated in subsequent tests using increasing multiples of the $ED_{50}$ determined in test (b) until the heart rate (HR) reaches or exceeds 500 beats per minute allowing the dose ($D_{500}$) necessary to produce a heart rate of 500 b.p.m. to be calculated. The ratio of $D_{500}$ to $ED_{50}$ in test (b) provides a measure of the selectivity (SI) of the compound for BAT as opposed to the cardio-vascular system. Compounds are considered to have significant selectivity which have an SI of >1. Non-selective compound have an SI of <1 (for example isoprenaline=0.06).

In the above tests, the laevorotatory optically active (S) form of the compound of formula I as its free base produced the following effects without any overt toxicity:

(a) 0.9° C. rise in core temperature at 10 mg/kg sub-cutaneously (s.c.);

(b) $ED_{50}$ 0.43 mg/kg s.c. 1.31 mg/kg p.o.;

(c) $D_{500}$: >63 mg/kg s.c.; SI>146.

The effects on obesity may be demonstrated in laboratory animals using, for example, Zucker rats or gold-thioglucose treated mice, using standard procedures.

When used for the treatment of obesity and/or related conditions (such as obesity associated with maturity onset diabetes) in warm-blooded animals (including man), the therapeutic agent (that is the compound of formula I in racemic (R,S) or, more preferably, laevorotatory optically active (S) form, or as a pharmaceutically acceptable salt thereof) will generally be administered at a daily oral dose in the range 0.25 to 10 mg/kg and, more preferably, 0.25 to 5 mg/kg is received, given as necessary in divided doses. However, the precise amount of therapeutic agent administered will necessarily be varied according to standard medical practice to take account of the age, weight and sex of the patient and of the severity of the condition under treatment.

The therapeutic agent will generally be administered as a suitable formulation, for example as a tablet, capsule, pill, powder, solution or suspension, for oral administration; or as a sterile solution, suspension or emulsion for parenteral administration. Similar formulations may be used for the veterinary treatment of obesity and/or related conditions.

When used for the modification of carcass composition, for example for the alteration of the ratio of fat to lean meat in meat producing animals (such as cattle, pigs, sheep, goats and rabbits), the therapeutic agent (as defined above) will generally be administered in the feed or drinking water of the animals using conventional procedures such that the animals receive a daily oral dose in the range, for example, 0.25 to 15 mg/kg and, preferably, 0.25–5 mg/kg, is received.

The following Preparations illustrate the production of the active ingredient for the therapeutic agents of the invention:

PREPARATION 1

A mixture of (−)-N-[2-hydroxy-3-phenoxypropyl]-N-(2-isobutyramidoethyl)ammonium 2,3:4,6-di-O-isopropylidene-α-D-xylo-hexulosofuranosonate (also known as (−)-1-phenoxy-3-β-isobutyramidoethylamino-2-propanol (−)-2,3:4,6-di-O-isopropylidene-2-keto-L-gulonate and described in Example 31 of UK patent specification Ser. No. 1455116) (96 g) and 2M sodium hydroxide solution (500 ml) was extracted with methylene chloride (200 ml). The extracts were dried (MgSO$_4$) and the solvent evaporated. The residue was recrystallised twice from ethyl acetate to give crystalline (−)-N-(2-[2-hydroxy-3-phenoxypropyl]aminoethyl)isobutyramide as a white solid, m.p. 89°–91° C., $^{25}[\alpha]_D$-6.3° [c, 1.05; methanol]; microanalysis, $C_{15}H_{24}N_2O_3$ requires: C, 64.3; H, 8.60; N, 10.0%; found: C, 64.4; H, 8.5; N, 9.8%.

PREPARATION 2

A solution of (−)-N-(2-[2-hydroxy-3-phenoxypropyl]aminoethyl)isobutyramide (0.7 g) in anhydrous ether (10 ml) was treated with an excess of a saturated solution of hydrogen chloride in anhydrous ether. The solid which formed was collected and recrystallised twice from a mixture of methanol and anhydrous ether to give (−)-N-[2-hydroxy-3-phenoxypropyl]-N-(2-isobutyramidoethyl)ammonium chloride, m.p. 137°–139° C.; $^{25}[\alpha]_D$-19.7° [c, 1.135; methanol]; microanalysis $C_{15}H_{24}N_2O_3$.HCl requires: C, 56.87; H, 7.90; N, 8.84; Cl, 11.20%; found: C, 56.80; H, 8.0; N, 8.6; Cl, 11.1%.

PREPARATION 3

A mixture of (S)-1,2-epoxy-3-phenoxypropane (0.495 g.) and N-(2-aminoethyl)isobutyramide (0.429 g) in ethanol (25 ml) was heated under reflux for 48 hours. The reaction mixture was cooled and solvent removed by rotary evaporation in vacuo. The residual solid was purified by column chromatography on silica (Merck, Art. 7736) using 5% v/v methanol in dichloromethane as eluant. The solid thereby obtained was purified by recrystallisation from ethyl acetate to give (S)-N-(2-[2-hydroxy-3-phenoxypropyl]aminoethyl)isobutyramide (0.425), m.p. 88°–89° C., $^{24}[\alpha]_D$-5.8° [c, 1.04; methanol], mixed m.p. with material from Preparation 1, 88°–89° C.

The starting (S)-1,2-epoxy-3-phenoxypropane may be obtained, for example, as described in European patent application, publication number 166527A2 or in *J. Amer. Chem. Soc.*, 1979, 101 (13), 3666–3668.

What is claimed is:

1. A method of treatment of obesity or diabetes mellitus in a warm-blooded animal requiring such treatment which comprises administering to said animal an amount of the compound N-(2-[2-hydroxy-3-phenoxypropyl]aminoethyl)isobutyramide in racemic (R,S) or laevorotatory optically active (S) form, or of a pharmaceutically acceptable acid-addition salt thereof, sufficient to increase thermogenesis.

2. A method as claimed in claim 1 wherein the laevorotatory optically active (S) form of the compound or a pharmaceutically acceptable acid-addition salt defined in claim 1 is administered.

3. A method as claimed in claim 1 wherein a pharmaceutically acceptable acid-addition salt of the compound defined in claim 1 is administered.

4. A method as claimed in claim 3 wherein the salt administered is selected from the hydrochloride, hydrobromide, citrate and D-gluconate salts.

5. A method as claimed in claim 1 wherein the compound or salt defined in claim 1 is administered orally at a daily dose in the range 0.25 to 10 mg/kg.

6. A method for the alteration of the ratio of fat to lean meat in meat producing animals which comprises administering to the animals an amount of the compound N-(2-[2-hydroxy-3-phenoxypropyl]aminoethyl)-isobutyramide in racemic (R,S) or levorotatory optically active (S) form, or of a pharmaceutically acceptable acid-addition salt thereof, sufficient to increase thermogenesis.

7. A method of increasing thermogenesis in a warm blooded animal in need of such increase which comprises administering to said warm blooded animal an amount of the compound N-(2-[2-hydroxy-3-phenoxypropyl]aminoethyl)isobutyramide in racemic (R,S) or levorotatory optically active (S) form, or of a pharmaceutically acceptable acid-addition of salt thereof, sufficient to increase thermogenesis.

* * * * *